(12) United States Patent
Park et al.

(10) Patent No.: US 12,226,298 B2
(45) Date of Patent: Feb. 18, 2025

(54) MEDICAL DEVICE FOR CURING LIQUID BANDAGE AND METHOD FOR CURING LIQUID BANDAGE USING SAME

(71) Applicant: SEOUL VIOSYS CO., LTD., Ansan-si (KR)

(72) Inventors: Ki Yon Park, Ansan-si (KR); Eun Mi Choi, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 1283 days.

(21) Appl. No.: 16/464,295

(22) PCT Filed: Nov. 29, 2017

(86) PCT No.: PCT/KR2017/013754
§ 371 (c)(1),
(2) Date: Feb. 15, 2021

(87) PCT Pub. No.: WO2018/101720
PCT Pub. Date: Jun. 7, 2018

(65) Prior Publication Data
US 2023/0190545 A1    Jun. 22, 2023

(30) Foreign Application Priority Data

Nov. 29, 2016 (KR) .................. 10-2016-0160835
Nov. 28, 2017 (KR) .................. 10-2017-0159974

(51) Int. Cl.
*A61N 1/00* (2006.01)
*A61F 13/00* (2006.01)
(Continued)

(52) U.S. Cl.
CPC ...... *A61F 15/005* (2013.01); *A61F 13/00063* (2013.01)

(58) Field of Classification Search
None
See application file for complete search history.

(56) References Cited

U.S. PATENT DOCUMENTS 6,761,729 B2    7/2004   Babaev
8,888,829 B2 *  11/2014  Ward ................... A61N 5/0624
                                                          607/95
(Continued)

FOREIGN PATENT DOCUMENTS

CN         1644345       7/2005
CN       101097261       1/2008
(Continued)

OTHER PUBLICATIONS

Office Action dated Feb. 19, 2021, issued in Chinese Patent Application No. 201780084929.9.
(Continued)

*Primary Examiner* — Kim M Lewis
(74) *Attorney, Agent, or Firm* — Oblon, McClelland, Maier & Neustadt, L.L.P.

(57) ABSTRACT

A medical device for curing a liquid bandage including a body, an input unit disposed on an outer wall of the body and configured to receive a signal input from outside, a light source disposed at one end of the body and including a diode configured to emit UV light to cure the liquid bandage in response to a signal input to the input unit, a liquid bandage storage unit disposed inside the body to store the liquid bandage, a liquid bandage discharge unit disposed at the one end or the other end of the body and configured to discharge the liquid bandage from the liquid bandage storage unit, a lid configured to open or cover the liquid bandage discharge unit, and a light quantity controller configured to control a quantity of light emitted from the light source according to a signal sent from the input unit or preset data.

6 Claims, 13 Drawing Sheets

(51) Int. Cl.
*A61F 15/00* (2006.01)
*A61N 5/06* (2006.01)

(56) References Cited

U.S. PATENT DOCUMENTS

| | | | |
|---|---|---|---|
| 10,517,371 B2* | 12/2019 | Miller | A46B 15/0036 |
| 2003/0153961 A1* | 8/2003 | Babaev | A61B 18/203 |
| | | | 607/89 |
| 2015/0151138 A1 | 6/2015 | Gualandi et al. | |

FOREIGN PATENT DOCUMENTS

| | | | | |
|---|---|---|---|---|
| CN | 104582631 | 4/2015 | | |
| JP | 10-179613 | 7/1998 | | |
| JP | 2006-055337 | 3/2006 | | |
| JP | 2006-517810 | 8/2006 | | |
| KR | 10-2011-0083169 | 7/2011 | | |
| KR | 10-2015-0106466 | 9/2015 | | |
| WO | WO-2012142550 A2 * | 10/2012 | ........... | A61N 5/0624 |

OTHER PUBLICATIONS

International Search Report dated Mar. 23, 2018, issued in International Application No. PCT/KR2017/013754.

* cited by examiner

MEDICAL DEVICE FOR CURING LIQUID BANDAGE AND METHOD FOR CURING LIQUID BANDAGE USING SAME

CROSS REFERENCE TO RELATED APPLICATIONS

This application is a National Stage Entry of International Patent Application No. PCT/KR2017/013754, filed on Nov. 11, 2017, and claims priority from and the benefit of Korean Patent Application No. 10-2016-0160835, filed on Nov. 29, 2016, and Korean Patent Application No. 10-2017-0159974, filed on Nov. 28, 2017, each of which is incorporated by reference for all purposes as if fully set forth herein.

BACKGROUND

Field

Exemplary embodiments of the invention relate generally to a medical device for curing a liquid bandage and a method for curing a liquid bandage using the same.

Discussion of the Background

A liquid bandage is a product used for healing and protection of small wounds. Unlike a general bandage that is wrapped around the skin, the liquid bandage is a mixture of a volatile liquid and a polymer material, which forms a film when the liquid is volatized and the polymer material is remained.

The liquid bandage protects a wound from external environments, such as dusts and bacteria, while maintaining moisture therein.

Typical liquid bandages include a liquid bandage that includes water as a solvent and polyvinylpyrrolidone as a polymer, a liquid bandage that includes alcohol as a solvent and pyroxylin, nitrocellulose, or methyl acrylate isobutene monoisopropylmaleate as a polymer, a liquid bandage that includes hexamethyldisiloxane or isooctane as a solvent and an acryl, cyanoacrylate or siloxane polymer as a main raw material, and the like.

A conventional liquid bandage generally requires a predetermined period of time for curing after being applied to the wound. Furthermore, using a conventional liquid bandage generally requires an application of constant force around the wound in order to prevent the wound from being widened until the liquid bandage is completely cured. In addition, a typical liquid bandage is naturally cured, and thus, exhibits low bonding strength.

The above information disclosed in this Background section is only for understanding of the background of the inventive concepts, and, therefore, it may contain information that does not constitute prior art.

SUMMARY

Medical devices constructed according to exemplary embodiments of the invention are capable of quickly curing a liquid bandage applied to a wound, and a method for curing a liquid bandage using the same.

Medical devices according to exemplary embodiments for curing a liquid bandage are also capable of applying a liquid bandage and curing the liquid bandage at the same time, and a method for curing a liquid bandage using the same.

Additional features of the inventive concepts will be set forth in the description which follows, and in part will be apparent from the description, or may be learned by practice of the inventive concepts.

A medical device for curing a liquid bandage according to an exemplary embodiment includes an input unit receiving a signal input from outside, and a light source including a diode emitting UV light for curing the liquid bandage in response to the signal input to the input unit.

A method for curing a liquid bandage according to an exemplary embodiment include applying a liquid bandage; and curing the liquid bandage by irradiating the liquid bandage with UV light.

A medical device for curing a liquid bandage according to another exemplary embodiment includes an input unit receiving a signal input from outside, and a light source including a diode emitting UV light for curing the liquid bandage in response to the signal input to the input unit.

The medical device may further include a light quantity controller controlling quantity of light emitted from the light source, in which the input unit sends a light quantity control signal received from outside to the light quantity controller.

The medical device may further include a data storage unit storing preset data for previously setting the quantity of light.

The medical device may further include a display unit displaying at least one of the quantity of light and the preset data.

The medical device may further include a timer controlling a curing duration for which the light source emits UV light for curing.

The medical device may further include a data storage unit storing preset data for previously setting the curing duration.

The medical device may further include a display unit displaying at least one of the curing duration and the preset data.

The light source may further include a diode emitting UV light for sterilization.

The medical device may further include a timer controlling at least one of a sterilization duration for which the light source emits UV light for sterilization and a curing duration for which the light source emits UV light for curing.

The medical device may further include a data storage unit storing preset data for previously setting at least one of the curing duration and the sterilization duration.

The medical device may further include a display unit displaying at least one of the curing duration, the sterilization duration, and the preset data.

The medical device may further include a sensor adapted to detect operation failure of the medical device.

The medical device may further include a display unit displaying a signal relating to the operation failure detected by the sensor.

The medical device may further include a liquid bandage storage unit storing the liquid bandage and a liquid bandage discharge unit discharging the liquid bandage from the liquid bandage storage unit.

The medical device may further include an antiseptic storage unit storing an antiseptic and an antiseptic discharge unit discharging the antiseptic from the antiseptic storage unit.

The medical device may further include a skin determination unit determining a skin type to be irradiated with the UV light, a controller calculating quantity of UV light and a UV irradiation duration depending upon the skin type, a light quantity controller controlling quantity of UV light to be emitted from the light source depending upon the quantity of UV light calculated by the controller, and a timer controlling a duration for which the light source emits UV light depending upon the UV irradiation duration calculated by the controller.

The medical device may further include a curing measurement unit measuring a degree of curing of the liquid bandage, and a display unit outputting a signal indicating completion of curing of the liquid bandage upon determining by the curing measurement unit that curing of the liquid bandage is completed.

A method for curing a liquid bandage using a medical device for curing a liquid bandage according to another exemplary embodiment includes applying a liquid bandage, and curing the liquid bandage by irradiating the liquid bandage with UV light.

The method may further include presetting quantity of UV light for curing the liquid bandage, before curing the liquid bandage.

In presetting quantity of UV light, the quantity of light may be preset depending upon a composition or an application area of the liquid bandage.

The method may further include presetting a curing duration for which UV light is emitted, before curing the liquid bandage.

The method may further include applying the antiseptic before application of the liquid bandage.

The method may further include irradiating a skin portion to which the liquid bandage is to be applied with UV light for sterilization, before application of the liquid bandage.

The method may further include determining a skin type to be irradiated with UV light; and calculating quantity of UV light and a UV irradiation duration depending upon the skin type, before curing the liquid bandage.

The curing the liquid bandage may further include measuring a degree of curing of the liquid bandage, and outputting a signal indicating completion of curing of the liquid bandage if it is determined that curing of the liquid bandage is completed.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
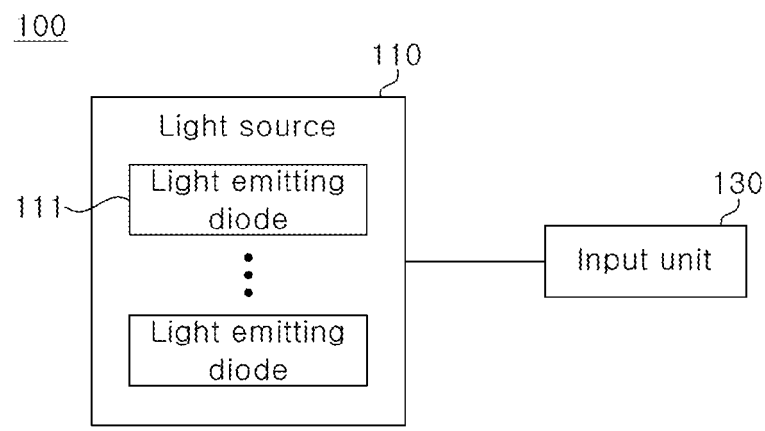
FIG. 1 is a block diagram of a medical device for curing a liquid bandage according to a first exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
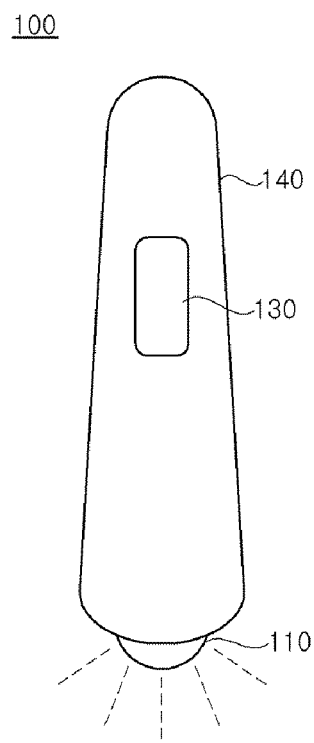
FIG. 2 and FIG. 3 are views of the medical device for curing a liquid bandage according to the first exemplary embodiment.
Figure 3:
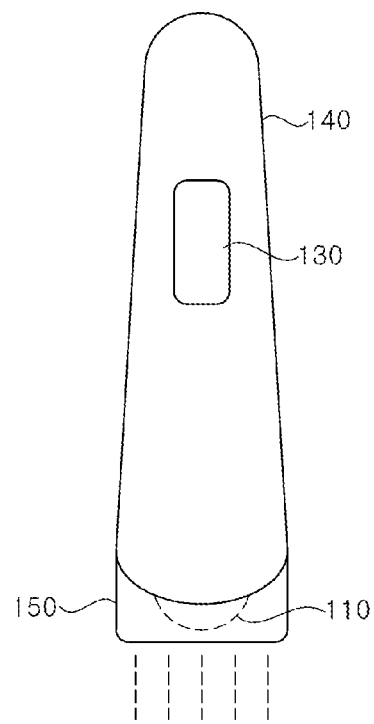

FIG. 1 is a block diagram of a medical device for curing a liquid bandage according to a first exemplary embodiment, and FIG. 2 and FIG. 3 are views of the medical device for curing a liquid bandage according to the first exemplary embodiment.

Referring to FIG. 1, a medical device 100 for curing a liquid bandage according to a first exemplary embodiment includes a light source 110 and an input unit 130.

The light source 110 emits UV light for curing a liquid bandage. The light source 110 includes a plurality of diodes 111 adapted to emit UV light for curing the liquid bandage. The diodes 111 may be light emitting diodes (LEDs) or laser diodes (LDs).

The input unit 130 acts as a switch connecting the light source 110 to a power supply unit. For example, when the input unit 130 receives a turn-on signal from outside, the input unit 130 electrically connects the light source 110 to the power supply unit. Then, the power supply unit supplies power to the light source 110 to emit UV light. In addition, when the input unit 130 receives a turn-off signal from outside, the input unit electrically disconnects the light source 110 from the power supply unit. Then, power supply from the power supply unit to the light source 110 is stopped and the light source 110 stops the emission of UV light.

According to an exemplary embodiment, the power supply unit may be disposed outside the medical device 100 or may be configured with a battery disposed inside the medical device 100.

Referring to FIG. 2, in the medical device 100 according to the first exemplary embodiment, the light source 110 is disposed at one end of a body 140 of the medical device 100, and the input unit 130 is disposed on an outer wall thereof. The input unit 130 is provided in the form of a button or a touchscreen. A portion of the input unit 130 may be exposed outside the body 140 and the other portion of the input unit 130 may be inserted into the body 140. The portion of the input unit 130 disposed inside the body 140 may be electrically connected to the light source 110. As such, when a signal is input to the input unit 130 through the exposed portion thereof, the light source 110 may receive power or be turned off.

Referring to FIG. 3, the medical device 100 includes a light guide 150 formed on the body 140. The light guide 150 is formed at one end of the body 140 at which the light source 110 is disposed. In addition, the light guide 150 is formed to surround a side surface of the light source 110.

The light guide 150 guides an irradiation direction of UV light emitted from the light source 110. As such, the light guide 150 guides the medical device 100 to emit UV light within a predetermined region.

As shown in FIG. 3, when the light guide 150 has a constant inner diameter, UV light is emitted within a range corresponding to the inner diameter of the light guide 150. If the inner diameter of the light guide 150 gradually increases with increasing distance between light guide 150 and the body 140, the UV irradiation range of the medical device 100 may also be increased.

According to the illustrated exemplary embodiment, the medical device 100 provides rapid curing of a liquid bandage on a target area by emitting UV light thereto. In this manner, the time for physical application of force to a wound may be omitted or reduced.

Figure 4:
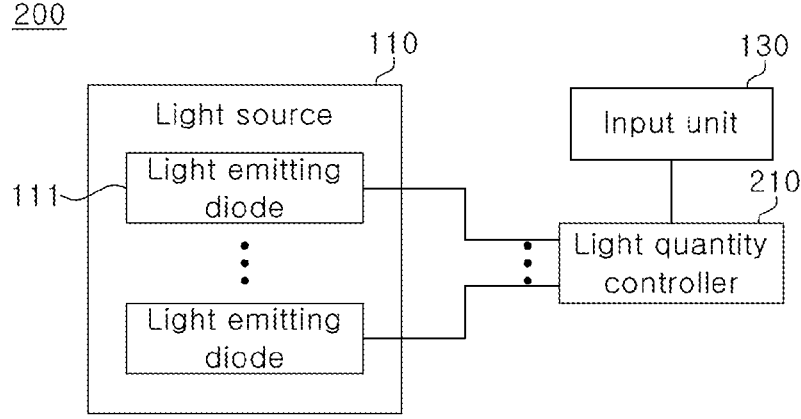
FIG. 4 is a block diagram of a medical device for curing a liquid bandage according to a second exemplary embodiment.

FIG. 4 is a block diagram of a medical device for curing a liquid bandage according to a second exemplary embodiment.

Referring to FIG. 4, a medical device 200 for curing a liquid bandage according to a second exemplary embodiment includes a light source 110, a light quantity controller 210, and an input unit 130.

The input unit 130 receives a light quantity control signal from outside. The input unit 130 sends the received light quantity control signal to the light quantity controller 210.

The light quantity controller 210 regulates the quantity of UV light emitted from the light source 110. For example, the light quantity controller 210 may regulate the quantity of UV light by controlling the number of diodes 111 emitting UV light among a plurality of diodes 111. The light quantity controller 210 sends a light emission signal to at least one of the diodes 111 in response to the light quantity control signal received from the input unit 130. Then, only the diode 111 receiving the light emission signal sent from the light quantity controller 210 emits light. Accordingly, the quantity of light is regulated in response to the light quantity control signal input to the input unit 130. The quantity of UV light may be changed depending upon a composition of the liquid bandage or an applied area of the liquid bandage.

The medical device 200 according to the second exemplary embodiment has substantially the same shape as the medical device shown in FIG. 2 and FIG. 3. Accordingly, a diagram of the medical device 200 according to the second exemplary embodiment is omitted herein, and the medical device 200 according to the second exemplary embodiment will be described with reference to FIG. 2 and FIG. 3.

The medical device 200 according to the second exemplary embodiment includes the light source 110 and the light quantity controller 210 disposed inside a body 140 thereof. Although the light source 110 is disposed inside the body 140, a light emitting portion of the light source is exposed outside. The light quantity controller 210 is disposed inside the body 140 to be electrically connected to the input unit 130 and the light source 110.

A portion of the input unit 130 may be exposed outside from the body 140, and the other portion of the input unit 130 may be inserted into the body 140. The portion of the input unit 130 disposed inside the body 140 may be electrically connected to the light quantity controller 210. Thus, a signal input through the exposed portion of the input unit 130 is sent to the light quantity controller 210 electrically connected thereto.

Figure 5:
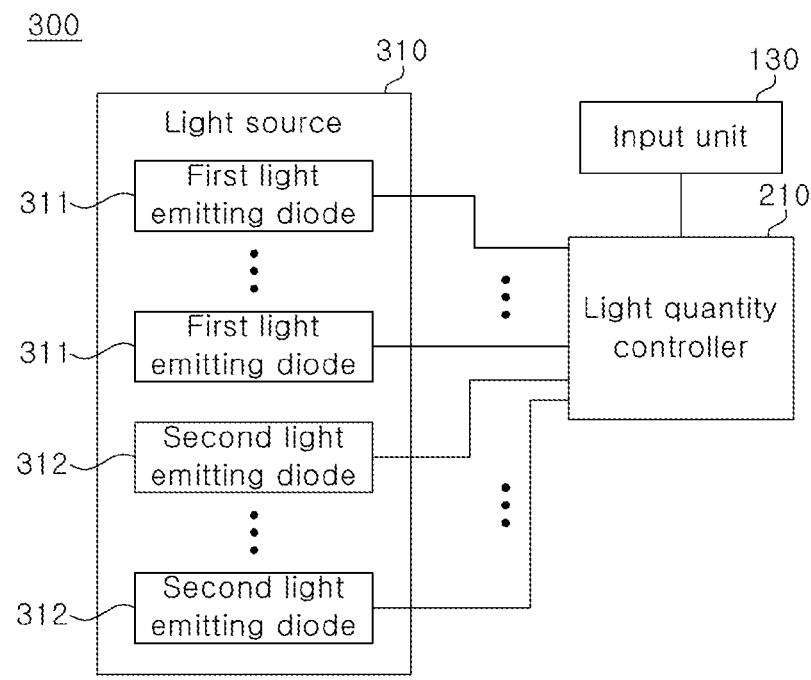
FIG. 5 is a block diagram of a medical device for curing a liquid bandage according to a third exemplary embodiment.

FIG. 5 is a block diagram of a medical device for curing a liquid bandage according to a third exemplary embodiment.

In a description of the medical device 300 for curing a liquid bandage according to the third exemplary embodiment, a repeated description of substantially the same components as those of the medical device for curing a liquid bandage according to the first exemplary embodiment will be omitted to avoid redundancy.

A light source 310 includes a plurality of first diodes 311 and at least one second diode 312. FIG. 5 shows that the light source 310 includes a plurality of second diodes 312. However, in some exemplary embodiments, the light source 310 may include a single second diode 312. The plural first diodes 311 emit UV light for curing of a liquid bandage. In addition, the second diode 312 emits UV light for sterilization of a wound.

The light quantity controller 210 controls the quantity of light of at least one of the first diodes 311 and the second diode 312.

The light quantity controller 210 sends a light emission signal to one type of diode selected from among the first diodes 311 and the second diode 312 in response to a signal received from the input unit 130. For example, when a sterilization function is selected through the input unit 130, the light quantity controller 210 sends a light emission signal to the second diode 312. In addition, when a curing function is selected through the input unit 130, the light quantity controller 210 sends the light emission signal to the first diodes 311.

Among the plurality of first diodes 311, a predetermined number of first diodes 311 is selected to emit light according to the light quantity control signal sent from the input unit 130. In addition, when a plurality of second diodes 312 is provided, a predetermined number of second diodes 312 is selected to emit light according to the light quantity control signal sent from the input unit 130.

In the illustrated exemplary embodiment, the light quantity controller 210 controls the quantity of light emitted from the light source 310 in response to a signal received from the input unit 130. However, in some exemplary embodiments, the medical device 300 may store preset data, such that the light quantity controller 210 can control the quantity of light emitted from the light source 310 according to the preset data.

Hereinafter, the first diode 311 and the second diode 312 of the light source 310 will not be separately illustrated in a description of the medical device for curing a liquid bandage. However, it should be understood that the diode of the light source may include the first diodes 311 or a combination of the first diode 311 and the second diode 312. Alternatively, a light source including the first diodes 311 and a light source including the second diodes 312 may be separately formed.

Figure 6:
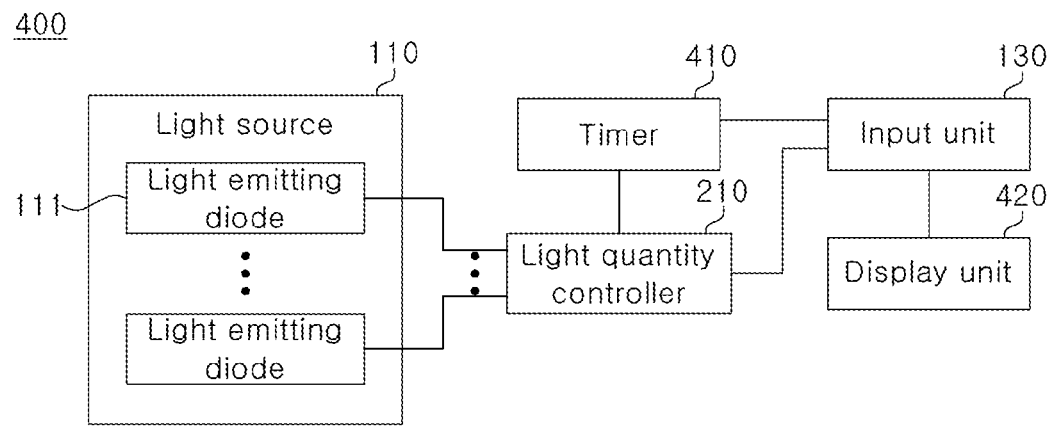
FIG. 6 is a block diagram of a medical device for curing a liquid bandage according to a fourth exemplary embodiment.
Figure 7:
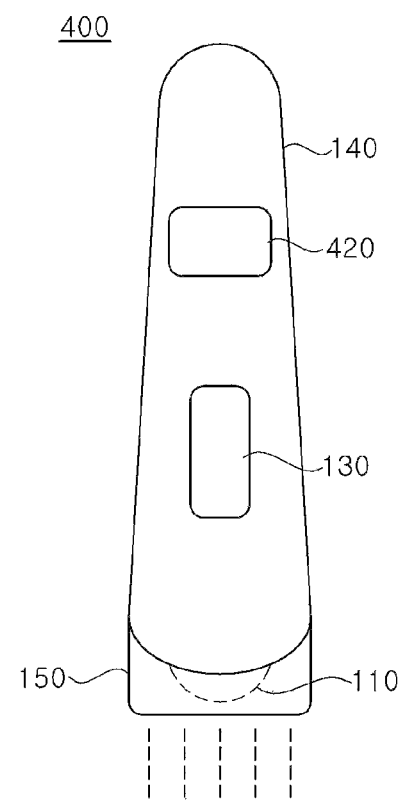
FIG. 7 is a view of the medical device for curing a liquid bandage according to the fourth exemplary embodiment.

FIG. 6 is a block diagram of a medical device for curing a liquid bandage according to a fourth exemplary embodiment, and FIG. 7 is a view of the medical device for curing a liquid bandage according to the fourth exemplary embodiment.

In a description of the medical device 400 for curing a liquid bandage according to the fourth exemplary embodiment, a repeated description of substantially the same components as those of the medical device for curing a liquid bandage according to the first to third exemplary embodiments will be omitted to avoid redundancy.

Referring to FIG. 6, the medical device 400 according to the fourth exemplary embodiment includes a light source 110, a light quantity controller 210, a timer 410, an input unit 130, and a display unit 420.

The timer 410 regulates a curing duration for which the light source 110 emits UV light. The timer 410 receives a time control signal sent from the input unit 130. The timer 410 sends a stop signal to the light quantity controller 210 when a predetermined period of time corresponding to the signal control signal elapses. In response to the stop signal sent from the timer 410, the light quantity controller 210 stops sending a light emission signal to the diode 111 or sends a light emission stop signal to the diode 111. Here, transmission of the light emission signal from the light quantity controller 210 to the diode 111 may be realized by power supply to the diode 111. Further, stop of the light emission signal or transmission of the light emission stop signal from the light quantity controller 210 to the diode 111 may be realized by stopping power supply to the diode 111.

In the illustrated exemplary embodiment, the medical device 400 is described as including the light source 110 including the diode 111 adapted to emit UV light for curing. However, the inventive concepts are not limited thereto, and in some exemplary embodiments, the medical device 400 may include the light source 310 of FIG. 5. The light source 310 of FIG. 5 according to the third exemplary embodiment includes the first diodes 311 for curing and the second diode 312 for sterilization. Here, the timer 410 is capable of regulating not only the curing duration but also a sterilization duration for which the light source emits UV light.

The input unit 130 receives control signals sent from the timer 410 and the light quantity controller 210. The input unit 130 generates a light quantity control signal and a time control signal in response to the received signals. The input unit 130 sends the light quantity control signal to the light quantity controller 210 and sends the time control signal to the timer 410.

The display unit 420 displays information on the signals input from the input unit 130, such that input of the signals can be confirmed from the outside.

In the illustrated exemplary embodiment, the timer 410 is described as controlling a UV emission duration of the light source 110 in response to the signals sent from the input unit 130. However, the inventive concepts are not limited thereto, and in some exemplary embodiments, the timer 410 may control the UV emission duration of the light source 110 according to preset data previously stored in the medical device 400. When the light source 110 includes the first diode 311 (see FIG. 5) and the second diode 312 (see FIG. 5), the timer 410 may control the UV emission duration of at least one of the first diode and the second diode.

Referring to FIG. 7, in the medical device 400 for curing a liquid bandage, the light source 110, the light quantity controller 210, and the timer 410 are disposed inside the body 140, and the input unit 130 and the display unit 420 are formed on the outer surface of the body 140. Further, the body 140 is formed at one end thereof with a light guide 150. In some exemplary embodiments, the light guide 150 may be omitted.

Figure 8:
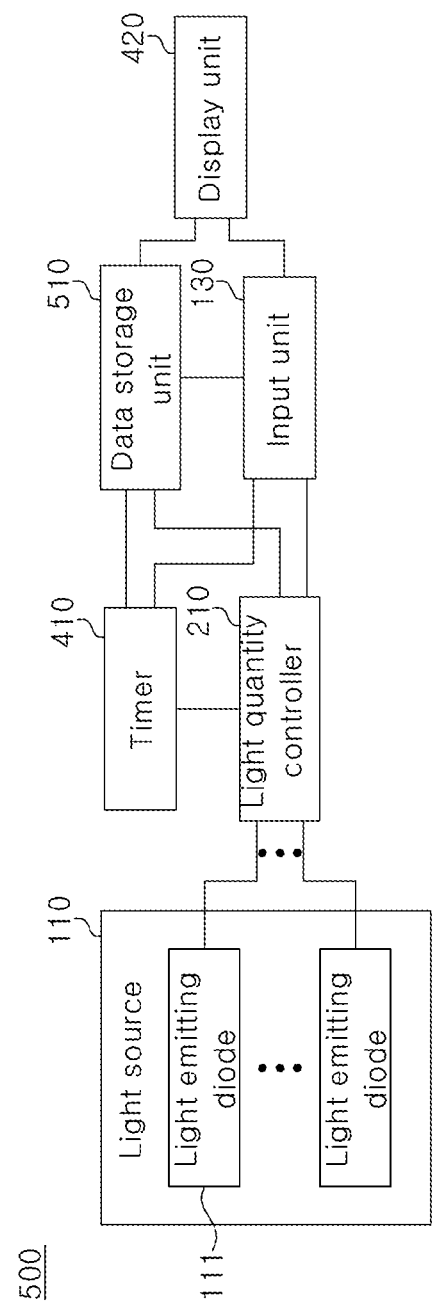
FIG. 8 is a block diagram of a medical device for curing a liquid bandage according to a fifth exemplary embodiment.

FIG. 8 is a block diagram of a medical device for curing a liquid bandage according to a fifth exemplary embodiment.

In a description of the medical device 500 for curing a liquid bandage according to the fifth exemplary embodiment, a repeated description of substantially the same components as those of the medical device for curing a liquid bandage according to the first to fourth exemplary embodiments will be omitted to avoid redundancy.

Referring to FIG. 8, the medical device 500 according to the fifth exemplary embodiment includes an input unit 130, a display unit 420, a light source 110, a light quantity controller 210, a timer 410, and a data storage unit 510.

The data storage unit 510 stores preset data related to a UV curing duration and the quantity of UV light. The preset data includes time data for setting UV curing duration and light quantity data for setting the quantity of UV light. The input unit 130 may select at least one of the time data and the light quantity data previously stored in the data storage unit 510.

For example, when certain time data is selected among the time data previously stored in the data storage unit 510 through the input unit 130, the data storage unit 510 sends a time setting signal corresponding to the selected time data to the timer 410. In addition, when certain light quantity data is selected among the light quantity data previously stored in the data storage unit 510 through the input unit 130, the data storage unit 510 sends a light quantity setting signal corresponding to the selected light quantity data the light quantity controller 210.

The time data and the light quantity data selected through the input unit 130 are displayed on the display unit 420.

In the medical device 500 according to the fifth exemplary embodiment, the data storage unit 510 is disposed inside the body 140 (see FIG. 7). Accordingly, the medical device 500 has substantially the same outer surface as that shown in FIG. 7.

The data storage unit 510, the light quantity controller 210, and the timer 410 may be formed on a single circuit board. Alternatively, the data storage unit 510, the light quantity controller 210, and the timer 410 may be individually formed on different circuit boards and disposed inside the body 140 (see FIG. 7).

Figure 9:
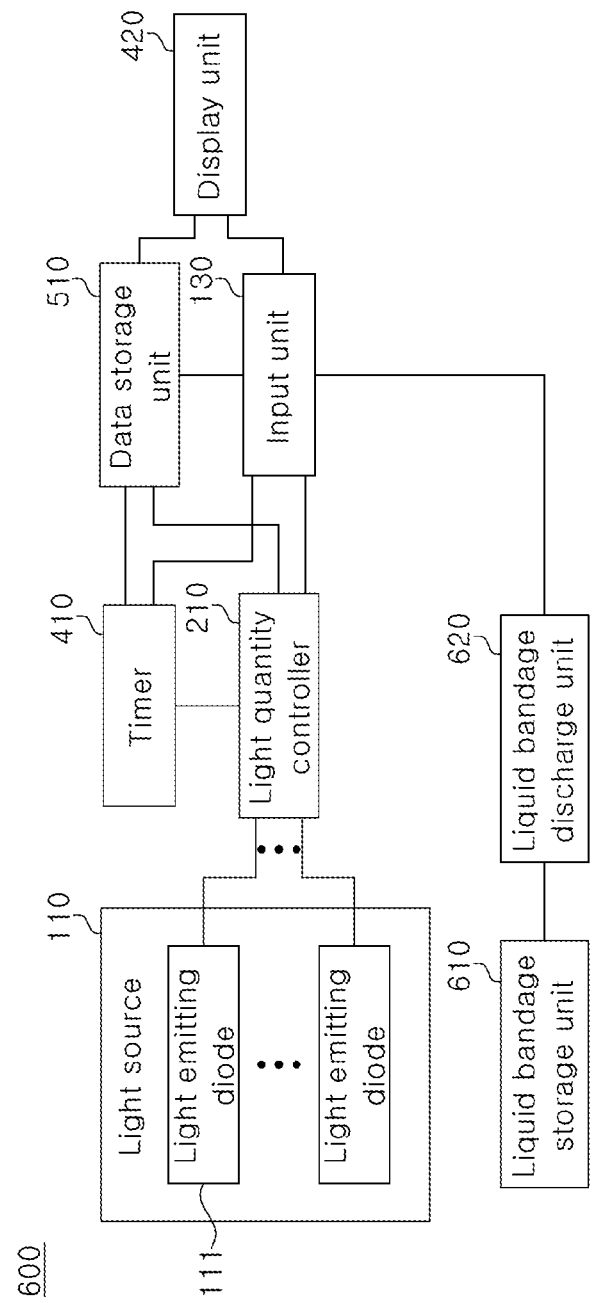
FIG. 9 is a block diagram of a medical device for curing a liquid bandage according to a sixth exemplary embodiment.
Figure 10:
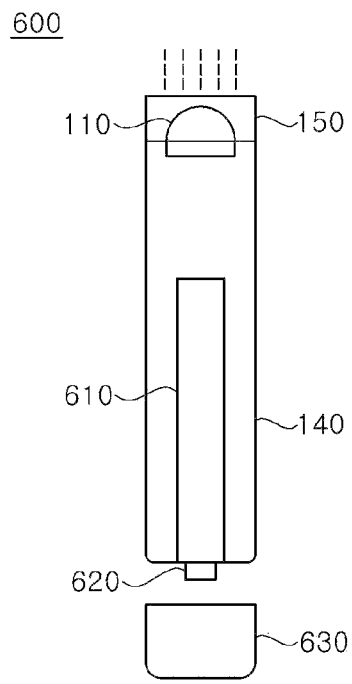
FIG. 10 and FIG. 11 are views of the medical device for curing a liquid bandage according to the sixth exemplary embodiment.
Figure 11:
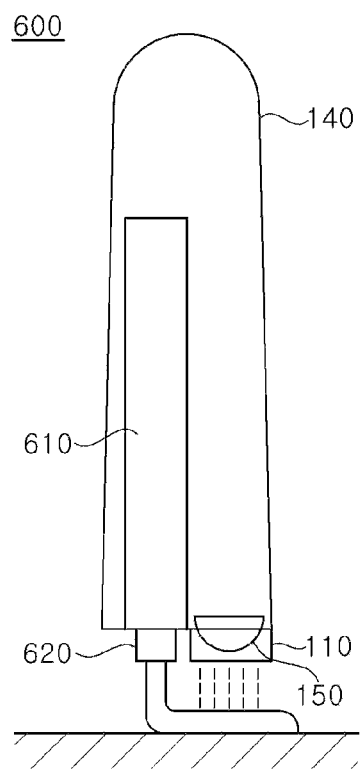

FIG. 9 is a block diagram of a medical device for curing a liquid bandage according to a sixth exemplary embodiment, and FIG. 10 and FIG. 11 are views of the medical device for curing a liquid bandage according to the sixth exemplary embodiment.

In a description of the medical device 600 for curing a liquid bandage according to the sixth embodiment, a repeated description of substantially the same components as those of the medical device for curing a liquid bandage according to the first to fifth exemplary embodiments will be omitted to avoid redundancy.

Referring to FIG. 9, the medical device 600 according to the sixth exemplary embodiment includes an input unit 130, a display unit 420, a light source 110, a light quantity controller 210, a timer 410, a data storage unit 510, a liquid bandage storage unit 610, and a liquid bandage discharge unit 620.

The liquid bandage storage unit 610 stores a liquid bandage. The liquid bandage may be used to suture a wounded portion or to protect the wounded portion from an external environment. The liquid bandage may be applied in a liquid state to the wounded portion, which may then be cured to suture or cover the wounded portion.

The liquid bandage discharge unit 620 receives a liquid bandage discharge start signal and a liquid bandage discharge stop signal from the input unit 130. The liquid bandage discharge unit 620 discharges the liquid bandage from the liquid bandage storage unit 610 in response to the liquid bandage discharge start signal. In addition, the liquid bandage discharge unit 620 stops discharge of the liquid bandage in response to the liquid bandage discharge stop signal.

In this manner, when the liquid bandage is discharged from the liquid bandage storage unit, the light source 110 emits UV light to the liquid bandage on the wounded portion to cure the liquid bandage.

Referring to FIG. 10 and FIG. 11, in the medical device 600 according to the sixth exemplary embodiment, the liquid bandage storage unit 610 and the light source 110 are disposed inside the body 140. Further, the light guide 150 and the liquid bandage discharge unit 620 are disposed outside the body 140.

In FIG. 10 and FIG. 11, other components of the medical device 600, such as the input unit 130, the display unit 420, the light quantity controller 210, the timer 410, and the data storage unit 510 are not illustrated.

Referring to FIG. 10, in the medical device 600 for curing a liquid bandage, the liquid bandage discharge unit 620 is formed at one end of the body 140 and the light source 110 is formed at the other end of the body 140.

The liquid bandage discharge unit 620 is electrically or physically connected to the input unit 130 to open or close the liquid bandage storage unit 610 in response to a signal from the input unit 130. As such, the liquid bandage may be discharged from the liquid bandage storage unit 610 or discharge of the liquid bandage therefrom may be stopped. Alternatively, the liquid bandage discharge unit 620 may not be electrically or physically connected to the input unit 130. That is, even when the liquid bandage discharge unit 620 is not electrically or physically connected to the input unit 130, the liquid bandage discharge unit 620 may be opened or closed by external force. For example, the liquid bandage discharge unit 620 may be opened or closed by a lid 630 shown in FIG. 10 to allow or stop discharge of the liquid bandage. Referring to FIG. 11, in the medical device 600 for curing a liquid bandage, the liquid bandage discharge unit 620 and the light source 110 are formed at one end of the body 140 to face the same direction. Accordingly, the medical device 600 according to the illustrated exemplary embodiment can cure the liquid bandage applied to a wounded portion while applying the liquid bandage to the wounded portion using the liquid bandage discharge unit 620. That is, application and curing of the liquid bandage can be performed at substantially the same time.

In the seventh exemplary embodiment, the liquid bandage is described as being stored in a liquid state in the liquid bandage storage unit 610. Alternatively, in some exemplary embodiments, the liquid bandage storage unit 610 may store individually packaged disposable liquid bandages therein. The individually packaged disposable liquid bandages may be inserted into the liquid bandage storage unit 610 and then a package of a liquid bandage is individually unpacked to allow the liquid bandage to be discharged through the liquid bandage discharge unit 620. The package of the liquid bandage may be unpacked inside the liquid bandage storage unit 610 or the liquid bandage discharge unit 620 to be discharged therefrom by various methods known in the art, for example, physical compression, cutting with a sharp component, and the like.

Figure 12:
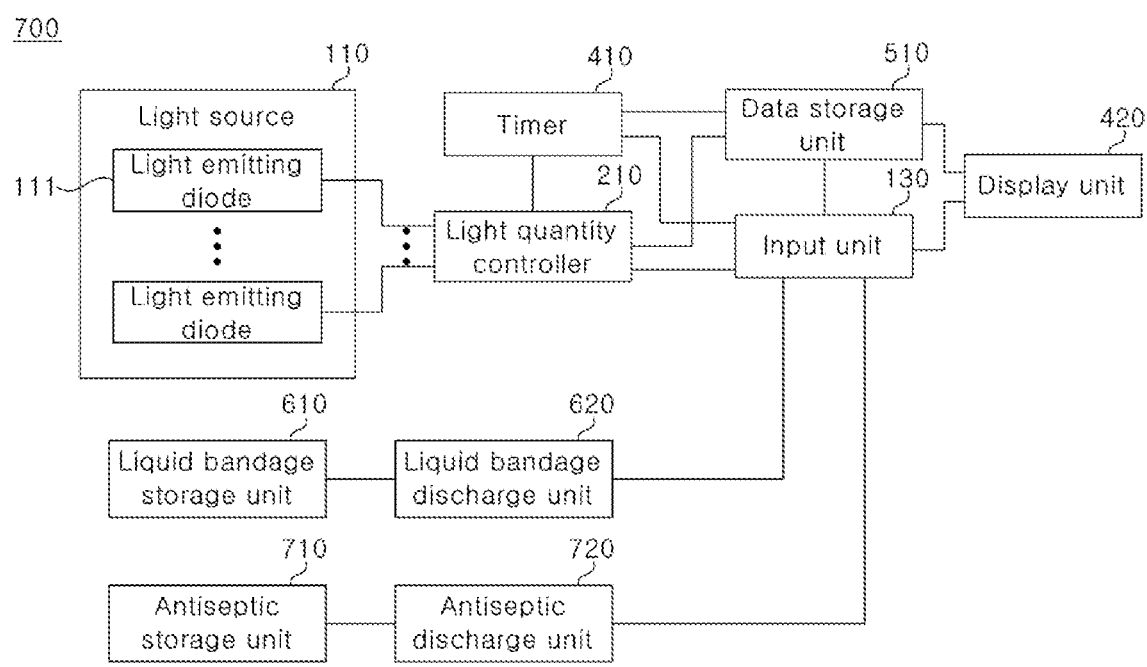
FIG. 12 is a block diagram of a medical device for curing a liquid bandage according to a seventh exemplary embodiment.
Figure 13:
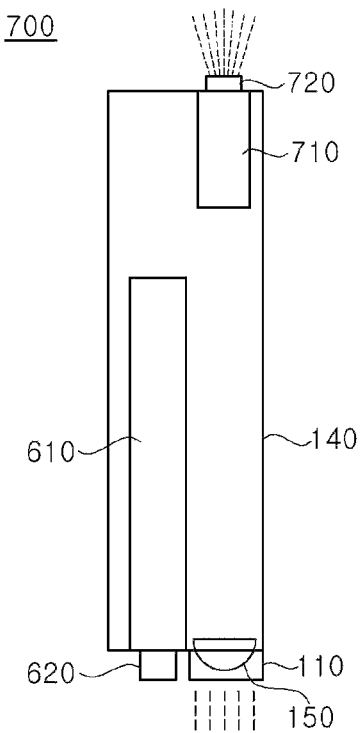
FIG. 13 and FIG. 14 are views of the medical device for curing a liquid bandage according to the seventh exemplary embodiment.
Figure 14:
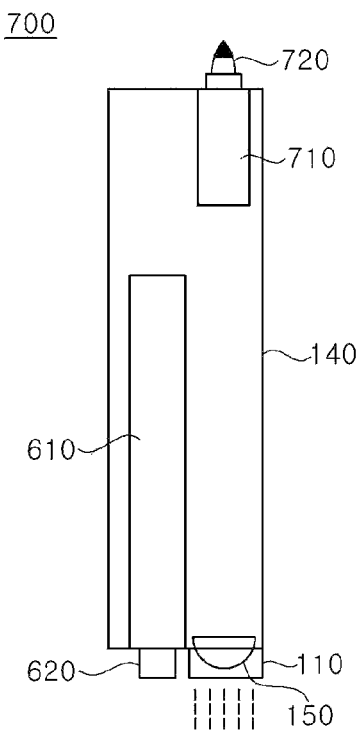

FIG. 12 is a block diagram of a medical device for curing a liquid bandage according to a seventh exemplary embodiment, and FIG. 13 and FIG. 14 are views of the medical device for curing a liquid bandage according to the seventh exemplary embodiment.

In a description of the medical device 700 for curing a liquid bandage according to the seventh exemplary embodiment, a repeated description of substantially the same components as those of the medical device for curing a liquid bandage according to the first to sixth exemplary embodiments will be omitted to avoid redundancy.

Referring to FIG. 12, the medical device 700 according to the seventh exemplary embodiment includes an input unit 130, a display unit 420, a light source 110, a light quantity controller 210, a timer 410, a data storage unit 510, a liquid bandage storage unit 610, a liquid bandage discharge unit 620, an antiseptic storage unit 710, and an antiseptic discharge unit 720.

The antiseptic storage unit 710 stores an antiseptic. The antiseptic serves to disinfect a wounded portion before discharge of the liquid bandage.

The antiseptic discharge unit 720 receives an antiseptic discharge start signal and an antiseptic discharge stop signal from the input unit 130. The antiseptic discharge unit 720 discharges the antiseptic from the antiseptic storage unit 710 in response to the antiseptic discharge start signal. In addition, the antiseptic discharge unit 720 stops discharge of the antiseptic in response to the antiseptic discharge stop signal.

In the seventh exemplary embodiment, the liquid bandage discharge unit 620 and the antiseptic discharge unit 720 are described as being operated in response to the signals from the input unit 130. However, the inventive concepts are not limited thereto. For example, in some exemplary embodiments, the liquid bandage discharge unit 620 and the antiseptic discharge unit 720 may be realized by inlets for discharging the liquid bandage and the antiseptic and may be opened or closed by external force.

Referring to FIG. 13 and FIG. 14, in the medical device 700 according to the seventh exemplary embodiment, the liquid bandage storage unit 610, the light source 110, and the antiseptic storage unit 710 are disposed inside the body 140. Other components of the medical device 700 are not shown.

Referring to FIG. 13 and FIG. 14, in the medical device 700, the liquid bandage discharge unit 620 and the light source 110 are formed at one end of the body 140 to face the same direction. In addition, the antiseptic discharge unit 720 is formed at the other end of the body 140. However, the inventive concepts are not limited thereto, and the locations of the liquid bandage discharge unit 620, the light source 110, and the antiseptic discharge unit 720 may be variously changed as desired.

Referring to FIG. 13, the antiseptic discharge unit 720 is electrically or physically connected to the input unit 130 to open or close the antiseptic storage unit 710 in response to a signal from the input unit 130. As such, the antiseptic may be discharged from the antiseptic storage unit 710 or discharge of the antiseptic therefrom may be stopped. For example, the antiseptic discharge unit 720 may discharge the antiseptic to the outside in response to a signal sent from the input unit 130.

Alternatively, the antiseptic discharge unit 720 may not be electrically or physically connected to the input unit 130. In this case, a separate lid may be provided to the antiseptic discharge unit 720 to open or close the antiseptic discharge unit 720 to allow or stop discharge of the antiseptic.

Referring to FIG. 14, the antiseptic discharge unit 720 has a brush shape. The antiseptic discharge unit 720 having a brush shape is connected to the antiseptic storage unit 710, such that the antiseptic flows through the brush to be discharged to the outside. However, the inventive concepts are not limited thereto, and in some exemplary embodiments, the antiseptic discharge unit 720 may have any structure capable of discharging the antiseptic, such as a ball shape.

In the exemplary embodiments described above, signals related to operation of all components of the medical device, such as the quantity of light, the time, discharge of the liquid bandage, discharge of the antiseptic, and the like are illustrated as being input through a single input unit 130. However, the inventive concepts are not limited thereto, and in some exemplary embodiments, the input unit 130 may be provided in plural such that each of the input units receives a signal for operation of one or more components.

In addition, the medical device 700 for curing a liquid bandage according to exemplary embodiments is not limited to the first to seventh exemplary embodiments. That is, in some exemplary embodiments, the medical device 700 may include at least one of the timer 410, the data storage unit 510, the liquid bandage storage unit 610, the liquid bandage discharge unit 620, the antiseptic storage unit 710, and the antiseptic discharge unit 720 as needed.

Further, in the exemplary embodiments, the display unit 420 is described as displaying the quantity of light, the curing duration, preset data, and the like. However, information displayed on the display unit 420 is not limited thereto. For example, the medical device according to some exemplary embodiments may include at least one sensor adapted to detect operation failure. The sensor can detect operation failure of each component constituting the medical device for curing a liquid bandage. The sensor sends a signal regarding the detected operation failure to the display unit 420. The sensor for detecting operation failure of the components constituting the medical device for curing a liquid bandage may be included in the medical devices described above.

The display unit 420 may display various data including operation failure of components constituting the medical device.

Figure 15:
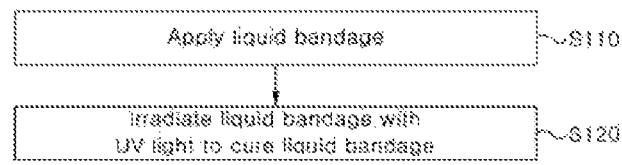
FIG. 15 is a flow diagram of a method for curing a liquid bandage according to an exemplary embodiment.

FIG. 15 is a flow diagram of a method for curing a liquid bandage according to an exemplary embodiment.

FIG. 15 is a flow diagram of the method for curing a liquid bandage using the medical device 100 for curing a liquid bandage according to the first exemplary embodiment.

Referring to FIG. 15, a liquid bandage is applied to a wounded portion (S110).

The liquid bandage is applied to the wounded portion using a device separate from the medical device for curing a liquid bandage. Alternatively, the liquid bandage may be stored in the medical device. The medical device may apply the liquid bandage stored therein to the wounded portion.

The liquid bandage is cured by irradiating the liquid bandage with UV light (S120).

The medical device emits UV light to the liquid bandage when the input unit receives a signal from outside. The liquid bandage is then irradiated with UV light to be rapidly cured thereby.

Since the liquid bandage has a liquid phase, the liquid bandage typically requires a predetermined period of time to be sufficiently cured to suture or seal a wounded portion. In addition, since the liquid bandage having the liquid phase has low bonding strength before curing, it is necessary to apply constant force to a portion near the wound in order to prevent the wound from being widened. However, according to the exemplary embodiment, by irradiating the liquid bandage with UV light, the duration of curing the liquid bandage can be reduced.

Figure 16:
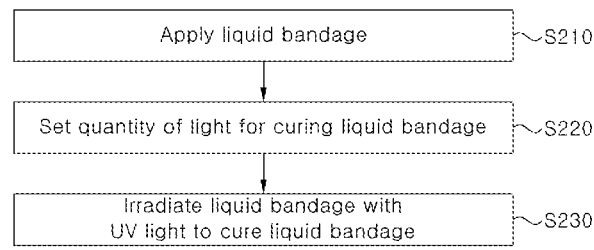
FIG. 16 is a flow diagram of a method for curing a liquid bandage according to another exemplary embodiment.

FIG. 16 is a flow diagram of a method for curing a liquid bandage according to another exemplary embodiment.

FIG. 16 is a flow diagram of the method for curing a liquid bandage using the medical device 100 for curing a liquid bandage according to the second exemplary embodiment.

Referring to FIG. 16, a liquid bandage is applied to a wounded portion (S210).

The liquid bandage is applied to the wounded portion using a device separate from the medical device for curing a liquid bandage. Alternatively, the liquid bandage may be stored in the medical device. The medical device may apply the liquid bandage stored therein to the wounded portion.

The quantity of light for curing the liquid bandage is set (S220).

The quantity of light for curing the liquid bandage may be set depending upon a material to which the liquid bandage is applied or an applied area of the liquid bandage. Here, the medical device may receive a signal related to the quantity of light for curing the liquid bandage through the input unit.

The liquid bandage is cured by irradiating the liquid bandage with UV light (S230)

The medical device emits UV light to the liquid bandage applied to the wounded portion. In this case, the medical device emits UV light to the liquid bandage with the quantity of light set in the previous step S220.

The liquid bandage is cured from a liquid phase to a solid phase upon irradiation with UV light.

Figure 17:
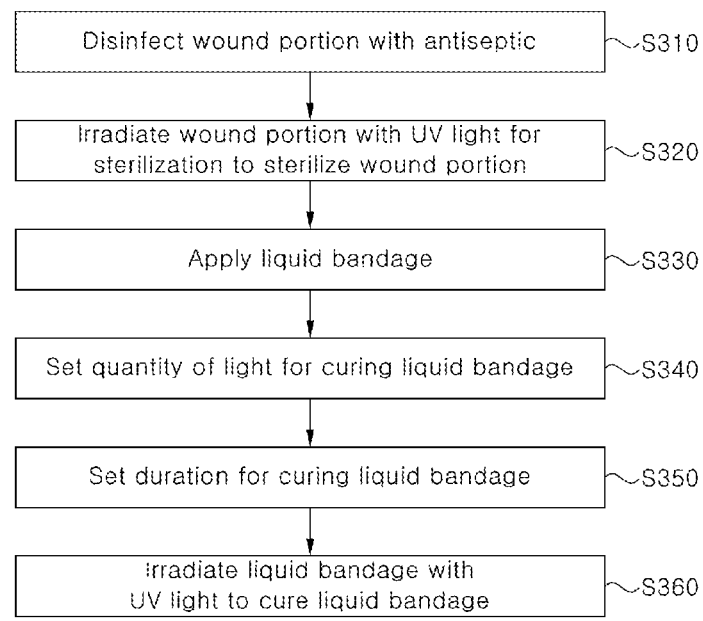
FIG. 17 is a flow diagram of a method for curing a liquid bandage according to yet another exemplary embodiment.

FIG. 17 is a flow diagram of a method for curing a liquid bandage according to yet another exemplary embodiment.

FIG. 17 is a flow diagram of the method for curing a liquid bandage using the medical device for curing a liquid bandage according to the seventh exemplary embodiment.

Referring to FIG. 17, an antiseptic is applied to a wounded portion (S310).

The medical device for curing a liquid bandage may include an antiseptic storage unit storing the antiseptic therein. The medical device may apply the antiseptic stored in the antiseptic storage unit to the wounded portion.

The wounded portion is sterilized by irradiating the wounded portion with UV light (S320).

The medical device may emit UV light not only for curing the liquid bandage but also for sterilization. The medical device may sterilize the wounded portion by irradiating the wound portion with UV light.

In this manner, the sterilizing step and the disinfecting step may be conducted to the wounded portion to prevent infection through the wound portion.

In some exemplary embodiments, the sequence of the sterilizing step and the disinfecting step may be changed as desired. In addition, in some exemplary embodiments, at least one of the sterilizing step and the disinfecting step may be omitted.

A liquid bandage is applied to the wounded portion (S330).

The liquid bandage is applied to the wounded portion using a device separate from the medical device for curing a liquid bandage. Alternatively, the liquid bandage may be stored in the medical device. The medical device may apply the liquid bandage stored therein to the wounded portion.

The quantity of light for curing the liquid bandage is set (S340).

More particularly, UV light for curing the liquid bandage is selected on the medical device for curing a liquid bandage. Then, the quantity of light to be emitted from the medical device for curing the liquid bandage may be set depending upon a material to which the liquid bandage is applied or an applied area of the liquid bandage. The quantity of light for curing the liquid bandage may be set through the input unit of the medical device.

A duration for curing the liquid bandage is set (S350).

A duration for which UV light for curing the liquid bandage is emitted to the liquid bandage is set. Accordingly, the medical device emits UV light for curing the liquid bandage only for the preset duration, and stops emission of UV light after the preset duration elapses. In this manner, the liquid bandage may be prevented from being excessively cured and power consumption may be reduced.

In the illustrated exemplary embodiment, the quantity of light and the duration for curing the liquid bandage are described as being set by a user. However, in some exemplary embodiments, the medical device for curing a liquid bandage may store preset data related to the quantity of light and the duration for curing the liquid bandage. Accordingly, the quantity of light and the duration for curing the liquid bandage may be set by selecting one of light quantity data and time data stored in the medical device for curing a liquid bandage.

The sequence of the step of selecting the quantity of light and the step of selecting the duration for curing the liquid bandage may be changed. In addition, in some exemplary embodiments, the step of selecting the duration for curing the liquid bandage may be omitted.

The liquid bandage is cured by irradiating the liquid bandage with UV light (S360).

The medical device emits UV light to the liquid bandage applied to the wounded portion. Here, the medical device emits UV light to the liquid bandage for the preset duration corresponding to the quantity of light set in the previous step.

Figure 18:
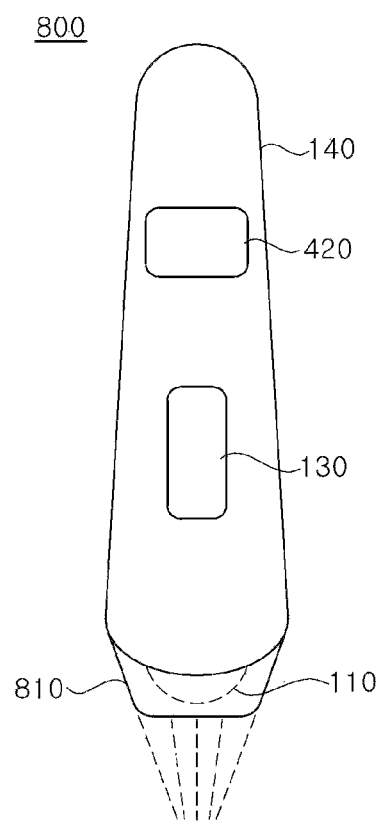
FIG. 18 is a view of a medical device for curing a liquid bandage according to an eighth exemplary embodiment.

FIG. 18 is a view of a medical device for curing a liquid bandage according to an eighth exemplary embodiment.

In a description of the medical device 800 for curing a liquid bandage according to the eighth exemplary embodiment, a repeated description of substantially the same components as those of the medical device for curing a liquid bandage according to the above exemplary embodiments will be omitted. In addition, the components of the medical device for curing a liquid bandage described above may also be applied to the medical device 800 for curing a liquid bandage according to the eighth exemplary embodiment in various ways.

Referring to FIG. 18, in the medical device 800 for curing a liquid bandage, the body 140 is formed with a light guide 810. The light guide 810 is formed at one end of the body 140 at which the light source 110 is disposed. The light guide 810 is formed to surround a side surface of the light source 110.

The light guide 810 guides an irradiation direction of UV light emitted from the light source 110. Referring to FIG. 18, an inner diameter of the light guide 810 gradually decreases with increasing distance from the body 140. Accordingly, UV light emitted from the light source 110 is emitted in a small region defined by the light guide 810. As such, the medical device 800 for curing a liquid bandage may intensively irradiate a portion covered with the liquid bandage with UV light while preventing a normal skin portion around the liquid bandage from being irradiated with UV light.

Figure 19:
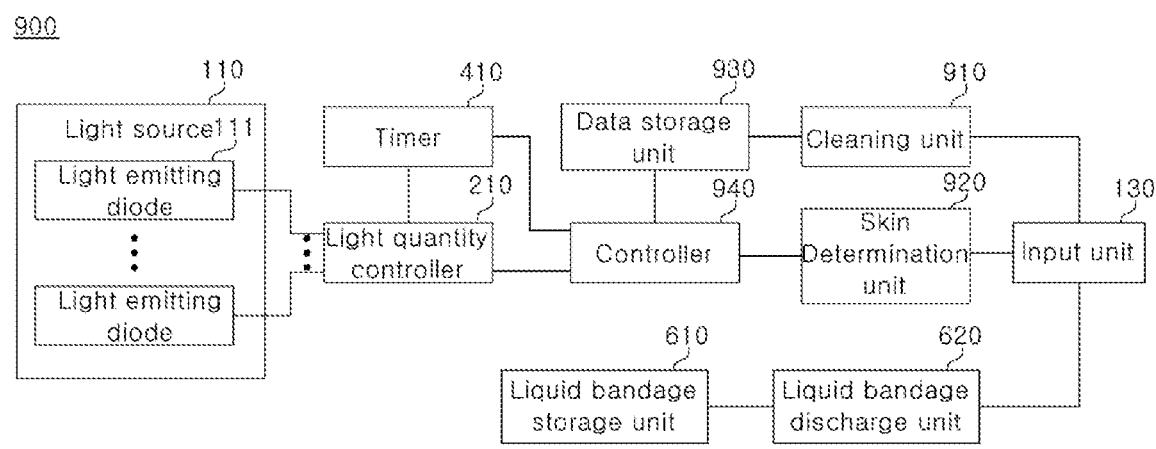
FIG. 19 is a block diagram of a medical device for curing a liquid bandage according to a ninth exemplary embodiment.

FIG. 19 is a block diagram of a medical device for curing a liquid bandage according to a ninth exemplary embodiment of the present disclosure.

In a description of the medical device 900 for curing a liquid bandage according to the ninth exemplary embodiment, a repeated description of substantially the same components as those of the medical device for curing a liquid bandage according to the above exemplary embodiments will be omitted.

Referring to FIG. 19, the medical device 900 includes an input unit 130, a light source 110, a cleaning unit 910, a skin determination unit 920, a controller 940, a data storage unit 930, a light quantity controller 210, a timer 410, a liquid bandage discharge unit 620, and a liquid bandage storage unit 610.

The cleaning unit 910 cleans the skin in a predetermined range so as to prevent foreign matter or contaminants from remaining on the skin. For example, the cleaning unit 910 may store a cleaning liquid such as water therein to spray the cleaning liquid outside the medical device 900 in response to a signal sent from the input unit 130. Alternatively, the cleaning unit 910 may spray air outside the medical device 900 in response to a signal sent from the input unit 130. The medical device 900 may remove foreign matter or contaminants from the skin by spraying the cleaning liquid or air toward the skin.

The skin determination unit 920 determines a skin type of normal skin. The skin determination unit 920 determines whether the skin has a bright color or a dark color by determining the skin type of normal skin. Specifically, the skin determination unit 920 may measure a degree of brightness of the normal skin. The skin determination unit 920 determines the skin type of a portion of the skin cleaned by the cleaning unit 910. Since determination of the skin type is performed on the portion of the skin cleaned by the cleaning unit 910, it is possible to accurately determine the skin type.

The skin type may be classified into a plurality of types depending upon skin color. Generally, the skin type is classified into Skin type 1 corresponding to a white color, Skin type 2 corresponding to a beige color, Skin type 3 corresponding to a bright brown color, Skin type 4 corresponding to a medium brown color, and Skin type 5 corresponding to a dark brown color and a black color.

The data storage unit 930 stores data regarding a UV irradiation duration corresponding to the quantity of UV light for each skin type. That is, the data storage unit 930 stores duration data for UV irradiation without damaging the skin, when the skin is irradiated with a certain quantity of UV light. In addition, the data storage unit 930 stores duration data for UV irradiation for each skin type.

The controller 940 compares the skin type determined by the skin determination unit 920 and the data stored in the data storage unit 930. Further, based on the result of comparison, the controller 940 calculates the quantity of UV light and the duration for UV irradiation without damaging the skin.

Figure 20:
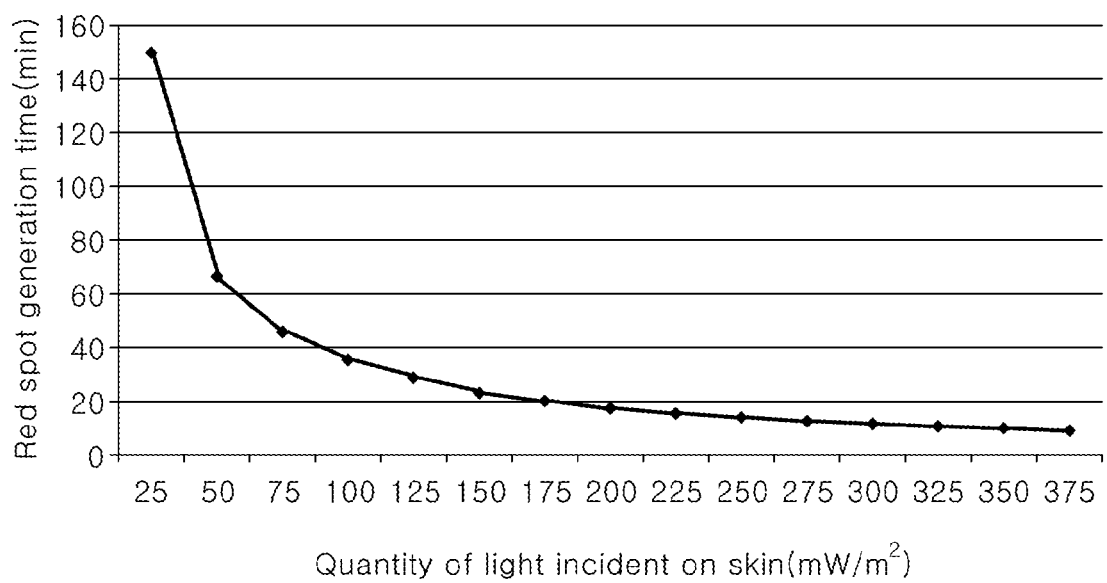
FIG. 20 is a graph depicting a relationship between red spot generation time and quantity of light applied to Skin type 2.

FIG. 20 is a graph depicting a relationship between red spot generation time and quantity of light applied to Skin type 2. As shown in FIG. 20, even for the same skin type, a red spot generation time is changed depending upon the quantity of light incident on the skin. In addition, since the degree of light absorbed by the skin is different depending upon the skin color, the red spot generation time can be changed depending upon the skin type even with the same quantity of light. Here, the red spot generation time may be used as a basis for determining the maximum duration for UV irradiation. The data storage unit 930 may store the red spot generation time or the maximum duration for UV irradiation depending upon the quantity of light for each skin type, as shown in FIG. 20. Here, the red spot generation time is exemplarily described as one factor to illustrate the duration for UV irradiation causing damage to the skin, and thus, the data controller 940 may not necessarily store data of the red spot generation. The data controller 940 may store data regarding the quantity of light and the UV irradiation duration causing other type damage to the skin by UV light.

The controller 940 sends a light quantity control signal corresponding to the calculated quantity of UV light to the light quantity controller 210. In addition, the controller 940 sends a time control signal corresponding to the calculated UV irradiation duration to the timer 410.

The light quantity controller 210 controls the quantity of light emitted from the light source 110 by controlling the light source 110 in response to the light quantity control signal.

Further, the timer 410 controls a duration for which the light source 110 emits UV light in response to the time control signal. The timer 410 may send a signal indicating a UV emission start time or a UV emission termination time to the light quantity controller 210. The light quantity controller 210 may control start or termination of UV emission of the light source 110 in response to the signal sent from the timer 410.

The liquid bandage storage unit 610 stores a liquid bandage. In addition, the liquid bandage discharge unit 620 discharges the liquid bandage from the liquid bandage storage unit 610. Although the medical device 900 according to the illustrated exemplary embodiment is described as including the liquid bandage storage unit 610 and the liquid bandage discharge unit 620, in some exemplary embodiments, however, these components may be omitted. That is, a liquid bandage may be applied to a wounded portion by a separate device and the medical device 900 may cure the liquid bandage applied to the wounded portion.

The medical device 900 according to the illustrated exemplary embodiment automatically regulates the quantity of UV light and the UV irradiation duration corresponding to the skin type of a user. Accordingly, the medical device 900 can prevent normal skin of the user from being damaged by UV light while curing the liquid bandage covering the wounded portion with UV light in consideration of the skin type of the user.

Figure 21:
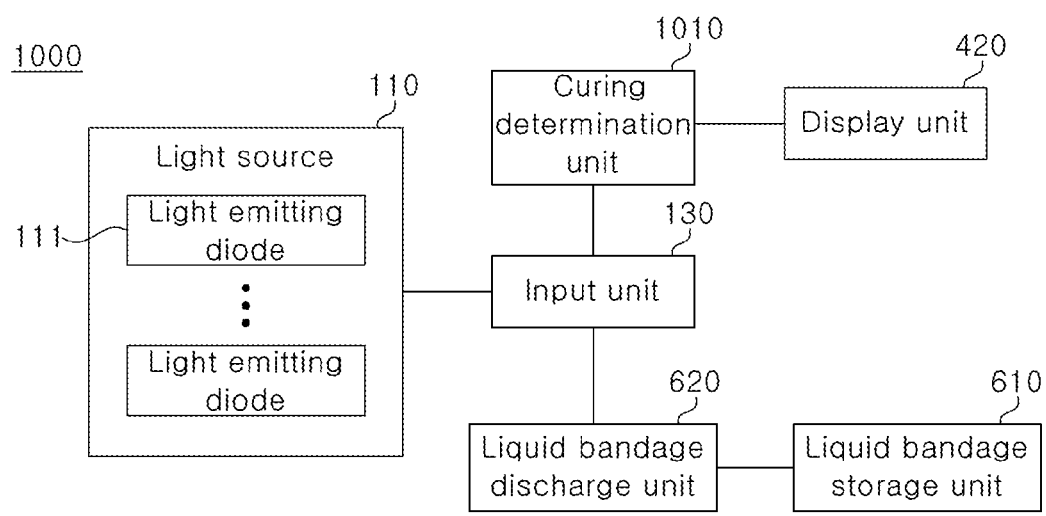
FIG. 21 is a block diagram of a medical device for curing a liquid bandage according to a tenth exemplary embodiment.

FIG. 21 is a block diagram of a medical device for curing a liquid bandage according to a tenth exemplary embodiment.

In a description of the medical device 1000 for curing a liquid bandage according to the tenth exemplary embodiment, a repeated description of substantially the same components as those of the medical device for curing a liquid bandage according to the above exemplary embodiments will be omitted to avoid redundancy.

Referring to FIG. 21, the medical device 1000 according to the illustrated exemplary embodiment includes an input unit 130, a light source 110, a liquid bandage discharge unit 620, a liquid bandage storage unit 610, a curing measurement unit 1010, and a display unit 420. In some exemplary embodiments, the liquid bandage discharge unit 620 and the liquid bandage storage unit 610 may be omitted.

The curing measurement unit 1010 measures the degree of curing of a liquid bandage covering a wounded portion to determine whether the liquid bandage is cured.

The degree of light scattering on a material depends upon the phase of the material having a gas phase, a liquid phase, or a solid phase. The curing measurement unit 1010 may measure the quantity of light reflected from the liquid bandage to determine the degree of curing of the liquid bandage. The curing measurement unit 1010 compares the quantity of reflected light measured thereby with a preset curing completion reference value to determine whether the liquid bandage is cured or not. Here, the curing measurement unit 1010 may measure the quantity of UV light emitted from the light source 110 and reflected from the liquid bandage. Alternatively, the curing measurement unit 1010 may include a separate light source to determine whether the liquid bandage is cured.

The curing measurement unit 1010 sends a curing completion signal to the display unit 420 when the measured degree of curing of the liquid bandage falls within a preset range.

In response to the curing completion signal from the curing measurement unit 1010, the display unit 420 outputs a signal corresponding thereto. The display unit 420 may visibly output the signal corresponding to curing completion using visible light or text, or may audibly output the signal using an alarm sound or the like. When the signal corresponding to corresponding to curing completion is output from the display unit 420, a user may move the medical device to another portion of the non-cured liquid bandage to cure the liquid bandage.

The medical device 1000 according to the illustrated exemplary embodiment determines whether the liquid bandage is cured and informs a user of the determination result, thereby preventing the skin of the user from being irradiated with UV light for unnecessary period of time. Further, when the liquid bandage is applied to the skin over a broad range, an uncured portion of the liquid bandage may be cured through UV irradiation using the medical device 1000. Accordingly, even when the liquid bandage is applied to the skin in a broad range, the entirety of the liquid bandage can be uniformly cured with efficiency.

In some exemplary embodiments, the medical device 1000 for curing a liquid bandage may further include a cleaning unit 910, a skin determination unit 920, and a data storage unit 930 described above. As such, the medical device 1000 may allow the liquid bandage to be cured through UV irradiation with the quantity of UV light for a period of time without causing damage to the normal skin.

The medical devices for curing a liquid bandage according to various exemplary embodiments include the input unit and the light source disposed on the body. In addition, each of the medical devices described above may include at least one of the light source, the light guide, the light quantity controller, the timer, the display unit, the data storage unit, the liquid bandage storage unit, the liquid bandage discharge unit, the antiseptic storage unit, the antiseptic discharge unit, the sensor, the cleaning unit, the skin determination unit, the controller, and the curing measurement unit. That is, the medical devices for curing a liquid bandage may include a combination of the above components. Further, the medical devices for curing a liquid bandage may perform various operations in association with these components therein.

The medical device and method for curing a liquid bandage according to exemplary embodiments can reduce a period of time for curing the liquid bandage. In addition, the medical device and method according to the exemplary embodiments can reduce or omit a time for physical application of force to a wounded portion through rapid curing of the liquid bandage.

Further, the medical device according to the exemplary embodiments allows both application of a liquid bandage and curing of the liquid bandage to be performed at the same time.

made by those skilled in the art without departing from the spirit and scope of the invention.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A medical device for curing a liquid bandage, comprising:
    a body;
    an input unit disposed on an outer wall of the body and configured to receive a signal input from outside;
    a light source disposed at one end of the body and comprising a diode configured to emit UV light to cure the liquid bandage in response to a signal input to the input unit;
    a liquid bandage storage unit disposed inside the body to store the liquid bandage;
    a liquid bandage discharge unit disposed at the one end or the other end of the body and configured to discharge the liquid bandage from the liquid bandage storage unit;
    a lid configured to open or cover the liquid bandage discharge unit; and
    a light quantity controller configured to control a quantity of light emitted from the light source according to a signal sent from the input unit or preset data.

2. The medical device for curing a liquid bandage according to claim 1, further comprising a timer configured to control a duration for which the light source emits UV light for curing according to the input unit or preset data.

3. The medical device for curing a liquid bandage according to claim 1, further comprising a sensor configured to detect operation failure of the medical device.

4. The medical device for curing a liquid bandage according to claim 1, further comprising a light guide disposed at the one end of the body to surround a side surface of the light source and guiding an irradiation direction or an irradiation range of the UV light.

5. The medical device for curing a liquid bandage according to claim 1, further comprising:
    a skin determination unit configured to determine a skin type to be irradiated with the UV light;
    a controller configured to calculate a quantity of UV light and a UV irradiation duration depending upon the skin type;
    a light quantity controller configured to control the quantity of UV light to be emitted from the light source depending upon the quantity of UV light calculated by the controller; and
    a timer configured to control a duration for which the light source emits UV light depending upon the UV irradiation duration calculated by the controller.

6. The medical device for curing a liquid bandage according to claim 1, further comprising:
    a curing measurement unit configured to measure a degree of the liquid bandage cured; and
    a display unit configured to output a signal indicating completion of curing of the liquid bandage upon determining by the curing measurement unit that curing of the liquid bandage is completed.

* * * * *